(12) United States Patent
Anand et al.

(10) Patent No.: US 10,004,479 B2
(45) Date of Patent: Jun. 26, 2018

(54) TEMPERATURE DISTRIBUTION DETERMINING APPARATUS

(71) Applicant: KONINKLIJKE PHILIPS N.V., Eindhoven (NL)

(72) Inventors: Ajay Anand, Fishkill, NY (US); Shriram Sethuraman, Briarcliff Manor, NY (US); Balasundar Iyyavu Raju, Chester, NY (US); Junbo Li, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 162 days.

(21) Appl. No.: 14/437,518

(22) PCT Filed: Nov. 11, 2013

(86) PCT No.: PCT/IB2013/060048
§ 371 (c)(1),
(2) Date: Apr. 22, 2015

(87) PCT Pub. No.: WO2014/076621
PCT Pub. Date: May 22, 2014

(65) Prior Publication Data
US 2015/0282786 A1    Oct. 8, 2015

Related U.S. Application Data

(60) Provisional application No. 61/727,789, filed on Nov. 19, 12.

(51) Int. Cl.
*A61B 8/08*    (2006.01)
*A61B 90/50*    (2016.01)
(Continued)

(52) U.S. Cl.
CPC ............ *A61B 8/5215* (2013.01); *A61B 5/015* (2013.01); *A61B 8/48* (2013.01); *A61B 8/485* (2013.01);
(Continued)

(58) Field of Classification Search
CPC .. A61B 8/00; A61B 90/00; A61B 5/00; A61B 18/00; A61B 2034/00; A61B 2090/00; A61B 2017/00; A61B 2018/00
See application file for complete search history.

(56) References Cited

U.S. PATENT DOCUMENTS 4,681,103 A * 7/1987 Boner .................. A61B 5/6864
600/461
5,224,492 A * 7/1993 Takahashi .............. A61B 5/015
600/10

(Continued)

FOREIGN PATENT DOCUMENTS

JP    H04352971 A    12/1992
JP    2001340350 A    12/2001
(Continued)

OTHER PUBLICATIONS

Anand, A. et al., "Three-dimensional spatial and temporal temperature imaging in gel phantoms using backscattered ultrasound", IEEE Transactions on Ultrasonics, Ferroelectrics and Frequency Control, 54(1), pp. 23 to 31, (2007).
(Continued)

*Primary Examiner* — Jennifer Dieterle
*Assistant Examiner* — Sean D Mattson

(57) ABSTRACT

The invention relates to a temperature distribution determining apparatus (21) for determining a temperature distribution within an object, to which energy is applied, by using an energy application element (2). A first temperature distribution is measured in a first region within a first temperature
(Continued)

range and a model describing a model temperature distribution in the first region and in a second region depending on modifiable model parameters is provided. A second temperature distribution is estimated in the second region within a second temperature range, while the energy is applied to the object, by modifying the model parameters such that a deviation of the model temperature distribution from the first temperature distribution in the first region is minimized. This allows considering the temperature dependence of the model parameters within the second temperature range, while estimating the second temperature distribution, thereby improving the accuracy of the estimation of the second temperature distribution.

15 Claims, 11 Drawing Sheets

(51) Int. Cl.
*A61B 5/01* (2006.01)
*A61B 8/00* (2006.01)
*A61B 18/14* (2006.01)
*A61B 90/00* (2016.01)
*A61B 34/10* (2016.01)
*A61B 8/06* (2006.01)
*A61B 18/00* (2006.01)
*A61B 17/00* (2006.01)

(52) U.S. Cl.
CPC .............. *A61B 8/5223* (2013.01); *A61B 8/58* (2013.01); *A61B 18/14* (2013.01); *A61B 90/50* (2016.02); *A61B 8/06* (2013.01); *A61B 8/483* (2013.01); *A61B 8/488* (2013.01); *A61B 8/543* (2013.01); *A61B 2017/00106* (2013.01); *A61B 2018/00791* (2013.01); *A61B 2034/104* (2016.02); *A61B 2090/378* (2016.02)

(56) References Cited

U.S. PATENT DOCUMENTS

| 6,423,002 | B1* | 7/2002 | Hossack | A61B 8/0833 |
| | | | | 128/916 |
| 8,016,757 | B2 | 9/2011 | Kaczkowski et al. | |
| 8,123,691 | B2 | 2/2012 | Mine et al. | |
| 2003/0171672 | A1 | 9/2003 | Varghese et al. | |
| 2005/0010209 | A1 | 1/2005 | Lee et al. | |
| 2005/0090742 | A1 | 4/2005 | Mine et al. | |
| 2006/0111706 | A1* | 5/2006 | Truckai | A61B 18/1477 |
| | | | | 606/41 |
| 2007/0106157 | A1* | 5/2007 | Kaczkowski | A61B 5/015 |
| | | | | 600/438 |
| 2007/0265609 | A1* | 11/2007 | Thapliyal | A61B 18/1492 |
| | | | | 606/27 |
| 2009/0182230 | A1 | 7/2009 | Liu et al. | |
| 2010/0036378 | A1 | 2/2010 | Savery et al. | |
| 2011/0060221 | A1* | 3/2011 | Fan | A61B 5/015 |
| | | | | 600/438 |
| 2012/0232388 | A1 | 9/2012 | Curra et al. | |
| 2013/0060243 | A1 | 3/2013 | Kuhn | |

FOREIGN PATENT DOCUMENTS

| WO | WO 2011091847 A1 * | 8/2011 | ............ A61B 5/015 |
| WO | WO 2011145020 A1 * | 11/2011 | ............ A61B 18/00 |

OTHER PUBLICATIONS

Pennes, H.H, "Analysis of tissue and arterial blood temperatures in the resting human forearm", 85:5-34, Journal of Applied Physiology, vol. 1, Aug. 1948, No. 2.

Pouch, A.M. et al. "In vivo noninvasive temperature measurement by B-Mode ultrasound imaging", American Institute of Ultrasound in Medicine, J Ultrasound Med 2010; 29:1595-1606.

Miller, N.R. et al., "Fundamental limitations of noninvasive temperature imaging by means of ultrasound echo strain estimation", Ultrasound in Med & Biol. vol. 28, No. 10, pp. 1319-1333, 2002.

* cited by examiner

TEMPERATURE DISTRIBUTION DETERMINING APPARATUS

CROSS-REFERENCE TO PRIOR APPLICATIONS

This application is the U.S. National Phase application under 35 U.S.C. § 371 of International Application Serial No. PCT/IB2013/060048, filed on Nov. 11, 2013, which claims the benefit of U.S. Application Ser. No. 61/727,789, filed on Nov. 19, 2012. These applications are hereby incorporated by reference herein.

FIELD OF THE INVENTION

The invention relates to a temperature distribution determining apparatus, a temperature distribution determining method and a computer program for determining a temperature distribution within an object caused by applying energy to the object. The invention relates further to a system for applying energy to the object comprising the temperature distribution determining apparatus.

BACKGROUND OF THE INVENTION

EP 2 387 963 A1 discloses a temperature distribution determining apparatus for determining a temperature distribution within an object caused by applying energy to the object. The apparatus comprises a temperature distribution measuring unit for measuring a spatially and temporally dependent first temperature distribution in the object, while the energy is applied to the object such that the object is heated to a temperature within a first temperature range. The apparatus further comprises a temperature distribution estimating unit for estimating a spatially and temporally dependent second temperature distribution in the object within a second temperature range, which is different to the first temperature range, based on the spatial and temporal dependence of the measured first temperature distribution.

SUMMARY OF THE INVENTION

It is an object of the present invention to provide a temperature distribution determining apparatus, a temperature distribution determining method and a computer program for determining a temperature within an object caused by applying energy to the object, which allows for an improved accuracy of the determined temperature distribution. It is a further object of the present invention to provide a system for applying energy to the object, which comprises the temperature distribution determining apparatus.

In a first aspect of the present invention a temperature distribution determining apparatus for determining a temperature distribution within an object caused by applying energy to the object is presented, wherein the energy is applied by using an energy application element and wherein the temperature distribution determining apparatus comprises:

a temperature distribution measuring unit for measuring a first temperature distribution in a first region within the object within a first temperature range, while the energy is applied to the object, a model providing unit for providing a model describing a model temperature distribution in the first region and in a second region within the object depending on modifiable model parameters, wherein the second region is closer to the energy application element than the first region, a temperature distribution estimating unit for estimating a second temperature distribution in the second region within a second temperature range, which is different from the first temperature range, while the energy is applied to the object, by modifying the model parameters such that a deviation of the model temperature distribution from the first temperature distribution in the first region is minimized.

Since the model parameters are modified during the application of the energy, the temperature dependence of the model parameters within the second temperature range can be considered, while estimating the second temperature distribution, thereby improving the accuracy of the estimation of the second temperature distribution. For instance, if the first temperature range includes temperatures below 50 degrees Celsius and if the second temperature range includes larger temperatures, the temperature dependence of the model parameters in the second, larger temperature range can be considered, while estimating the second temperature distribution, in order to improve the accuracy of determining the second temperature distribution.

The second temperature range is preferentially a temperature range, in which the temperature distribution measuring unit cannot measure a temperature distribution or not accurately measure a temperature distribution. For instance, if the temperature distribution measuring unit is adapted to perform an ultrasound thermometry procedure for measuring the temperature distribution, the second temperature range may include temperatures larger than 50 degrees Celsius and the first temperature range may include temperatures below 50 degrees Celsius.

The first temperature distribution can be a temporally and/or spatially dependent distribution. Preferentially, the first temperature distribution is a temporally and spatially dependent temperature distribution. Also the second temperature distribution can be a spatially and/or temporally dependent temperature distribution, wherein a spatially and temporally dependent temperature distribution is preferred.

The modifiable parameters, of which the temperature dependence also in the second temperature range can be considered during the estimation of the second temperature distribution, include preferentially thermal parameters like the thermal conductivity and/or electrical parameters like the electrical conductivity of the object. If the object is spatially inhomogeneous, also the modifiable parameters are preferentially spatially inhomogeneous, wherein the spatial inhomogeneity of the modifiable parameters corresponds to the spatial inhomogeneity of the object. For instance, the object can be a part of a living being comprising different elements like different kinds of tissue, blood vessels, et cetera, wherein for at least some of these different elements of the part of the living being different modifiable parameters can be provided by the model.

It is preferred that the energy application element is adapted to measure the temperature at the energy application element, wherein the provided model describes a model temperature distribution in the first and second regions and at the energy application element, wherein the temperature distribution estimating unit is adapted to modify the model parameters such that a deviation of the model temperature distribution from the first temperature distribution in the first region and from the temperature measured at the energy application element is minimized. By additionally considering the temperature measured at the energy application element the estimation of the second temperature distribution in the second region can be further improved.

Preferentially, the first region and the second region are adjacent regions such that the temperature distribution estimating unit can estimate an entire temperature distribution including at least the first and second temperature distributions. If the first and second regions are not adjacent regions and if there are further regions in between the first and second regions, the temperature distribution estimating unit is preferentially adapted to estimate an entire temperature distribution covering the first region, the second region and the regions in between the first and second regions.

It is also preferred that the model providing unit is adapted to initialize the provided model with initial model parameters, wherein at least one initial model parameter is an object-specific model parameter. For instance, if the object is a living being comprising blood vessels, the flow velocity within the blood vessels can be determined by, for instance, an ultrasound Doppler technique, wherein the flow velocity can be an initial model parameter, which is object-specific and which can be modified by the temperature distribution estimating unit for adapting the model to the first temperature distribution in the first region and optionally also to a temperature measured at the energy application element. Using initial object-specific model parameters can further improve the accuracy of estimating the second temperature distribution in the second temperature range.

In a preferred embodiment, the object is a living being and the energy is applied to the living being for ablating a part of the living being, wherein the temperature distribution determining apparatus further comprises an ablated region determining unit for determining an ablated region defining a region within the object that has been ablated, wherein the ablated region determining unit is adapted to determine the ablated region by determining a part of the object for which the estimated second temperature distribution comprises a temperature being larger than a predefined temperature threshold. This allows monitoring the ablation procedure by observing the development of the ablated region. The ablated region is preferentially shown on a display. On the display also a region of interest, which may be a tumor region and which should be ablated, can be shown. For example, an overlay of the ablated region and the region of interest can be shown on the display.

The living being is a person or an animal and the energy application element is preferentially a needle or a catheter being adapted to apply the energy. The energy is preferentially radio frequency (RF) energy such that the catheter or needle preferentially comprises a corresponding RF electrode. The region of interest is preferentially a tumor region, which should be ablated completely. By displaying the determined ablated region and the tumor region they can easily be compared by a physician performing the ablation procedure such that the physician can ensure that the ablated region completely covers the tumor region.

The temperature distribution measuring unit preferentially comprises an ultrasound probe for acquiring ultrasound data of the first region and an ultrasound thermometry unit for determining the temperature distribution based on the acquired ultrasound data. This allows measuring the first temperature distribution in the first region during the application of the energy in a technically not very complex way, in particular in comparison with known magnetic resonance based temperature distribution measuring devices.

The temperature distribution measuring unit is preferentially adapted such that the first region is formed by a plane. The first region can be formed by one or several planes, which may be vertical and/or horizontal. For instance, the ultrasound probe may be adapted to acquire the ultrasound data in two planes being orthogonal to each other and defining the first region. However, the first region may also be non-planar, in particular, curved.

Preferentially, the temperature distribution measuring unit comprises a fixture for fixing the ultrasound probe to the energy application element. The fixture has preferentially known dimensions such that, if the fixture attaches the ultrasound probe and the energy application element to each other, the spatial relation, in particular the distance, between the ultrasound probe and the energy application element is known. The fixture is preferentially adapted such that the temperature measuring unit measures the first temperature distribution in a first region, which has a distance to the energy application element that ensures that the first temperature distribution is measurable in the first region, i.e. which ensures that the first region is not too close to the energy application element.

In an embodiment the temperature distribution measuring unit is adapted to modify the first region depending on the measured first temperature distribution, in order to measure different first temperature distributions in different first regions in the first temperature range, wherein the model providing unit is adapted to provide the model such that it describes a model temperature distribution in the different first regions and in the second region within the object depending on the modifiable parameters and wherein the temperature distribution estimating unit is adapted to estimate the second temperature distribution in the second region within the second temperature range, while the energy is applied to the object, by modifying the model parameters such that a deviation of the model temperature distribution from the first temperature distributions in the first regions is minimized. Since the first region is modified depending on the measured first temperature distribution, in order to measure different first temperature distributions in different first regions, the first region can be adapted to the currently measured first distribution. This allows, for example, modifying the first region depending on an actually measured first temperature distribution such that in the modified first region, i.e. in the new first region, the measurement of the temperature of the object can be continued, if the temperature in the previous first region would be too high for being accurately measured, thereby extending the time period in which a first temperature distribution of the object can be measured.

Preferentially, the temperature distribution measuring unit is adapted to modify the first region by changing the position of the first region. In particular, the temperature distribution measuring unit may be adapted to consecutively locate the first region at different positions, wherein, if the position of the first region is changed, it is changed from a position being closer to the energy application element to a position being more distant to the energy application element. By providing different first regions having different distances to the energy application element the measurement of a temperature distribution can be continued in another first region being more distant to the energy application element than the current first region, when the temperature distribution measuring unit is not able anymore to measure the temperature in the current first region. Thus, by increasing the distance of the respective first region to the energy appplication element during the heating process the time period, during which the temperature of the object can be measured, can be increased very effectively in a relatively simple way.

The temperature distribution measuring unit may comprise an ultrasound probe and may be adapted to move the ultrasound probe for changing the position of the first region, in order to modify the first region. In this case the ultrasound probe is preferentially a one-dimensional ultrasound probe. This allows using a technically relatively simple ultrasound probe for measuring the temperature distribution in different first regions, which have different distances to the energy application element. The ultrasound probe may also be adapted such that the position of the first region is changeable without moving the ultrasound probe. In this case the ultrasound probe is preferentially a two-dimensional ultrasound probe. This allows providing the ultrasound probe without requiring a mechanical movement apparatus for moving the ultrasound probe relative to the energy application element, which can lead to a mechanically simpler temperature distribution measuring unit.

It is further preferred that the temperature distribution measuring unit is adapted such that the ultrasound probe acquires reference ultrasound data for the different first regions at reference temperatures and actual ultrasound data for the different first regions and that the ultrasound thermometry unit determines a first temperature distribution in a respective first region depending on respective actual ultrasound data acquired for the respective first region, the reference ultrasound data acquired for the respective first region and the respective reference temperature. In particular, the temperature distribution measuring unit is adapted such that in a reference data acquisition stage the ultrasound probe acquires the reference ultrasound data for the different first regions at known reference temperatures and that in a temperature distribution measurement stage the ultrasound probe acquires actual ultrasound data and the ultrasound thermometry unit determines the first temperature distributions in the different first regions depending on respective actual ultrasound data acquired for the respective first region, the reference ultrasound data acquired for the respective first region and the respective reference temperature. The reference temperature can be the same for each first region. For instance, if the object is a person, the reference temperature may be 37 degrees Celsius. In particular, if the energy application element is an ablation element for ablating a part of the person like a tumor, before the ablation procedure is started, in the reference data acquisition stage the ultrasound probe can acquire the reference ultrasound data, wherein in this case the person has a known temperature of about 37 degrees Celsius. Then, during the ablation procedure the first temperature distributions can be measured in the different first regions, without requiring an acquisition of reference data during the ablation procedure, thereby fast and accurately measuring the first temperature distributions during the ablation procedure by ultrasound thermometry.

In another preferred embodiment the model providing unit provides the model of the object such that it describes a model temperature distribution in the first regions, in which the respective first temperature distribution has been measured already, and in the first regions, in which the respective first temperature distribution has not been measured already, depending on modifiable model parameters, wherein the temperature distribution estimating unit determines the reference temperature for a respective first region, in which the respective first temperature distribution has not been measured already, by modifying the model parameters such that a deviation of the model temperature distribution in the first regions, in which the respective first temperature distribution has been measured already, from the measured first temperature distributions in the first regions, in which the respective first temperature distribution has been measured already, is minimized and by determining the reference temperature from the modified model. Thus, in this embodiment the first temperature distributions can be measured in the different first regions, without requiring an acquisition of reference ultrasound data at known reference temperatures in a previous reference data acquisition stage.

The temperature distribution measuring unit is preferentially adapted to determine whether the measured first temperature distribution in the first region includes a temperature outside a predefined temperature range and to modify the first region, if the measured first temperature distribution in the first region includes a temperature outside the predefined temperature range. The predefined temperature range may be similar to the first temperature range. For instance, the object may be a person or an animal and the predefined temperature range may be defined by an upper maximum temperature of 50 degrees Celsius. The predefined temperature range may be further defined by a lower minimum temperature being equal to the normal temperature of the person or animal, in particular, being 37 degrees Celsius.

In a further aspect of the present invention a system for applying energy to an object is presented, wherein the system comprises:

an energy application element for applying the energy to the object, and a temperature distribution determining apparatus for determining a temperature distribution within the object caused by applying the energy to the object as defined in claim 1.

In a preferred embodiment, the system further comprises an energy application control unit for controlling the energy application element depending on the determined temperature distribution. In particular, a region of interest, which should be ablated, like a tumor region can be provided and compared with a determined ablated region, wherein the ablated region can be determined depending on the determined temperature distribution. The energy application control unit can then be adapted to control the application of the energy such that the determined ablated region completely covers the region of interest, in order to ensure that the region of interest has been ablated completely. In this way the application of energy to the object can be improved.

In a further aspect of the present invention a temperature distribution determining method for determining a temperature distribution within an object caused by applying energy to the object is presented, wherein the energy is applied by using an energy application element and wherein the temperature distribution determining method comprises:

measuring a first temperature distribution in a first region within the object within a first temperature range, while the energy is applied to the object, by a temperature distribution measuring unit, providing a model describing a model temperature distribution in the first region and in a second region within the object depending on modifiable model parameters, wherein the second region is closer to the energy application element than the first region, by a model providing unit, estimating a second temperature distribution in the second region within a second temperature range, which is different from the first temperature range, while the energy is applied to the object, by modifying the model parameters such that a deviation of the model temperature distribution from the first temperature distribution in the first region is minimized by a temperature distribution estimating unit.

In a further aspect of the present invention a computer program for determining a temperature distribution within an object caused by applying energy to the object is presented, wherein the computer program comprises program code means for causing a temperature distribution determining apparatus as defined in claim 1 to carry out the steps of the temperature distribution determining method as defined in claim 14, when the computer program is run on a computer controlling the temperature distribution determining apparatus.

It shall be understood that the temperature distribution determining apparatus of claim 1, the system of claim 12, the temperature distribution determining method of claim 14 and the computer program of claim 15 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
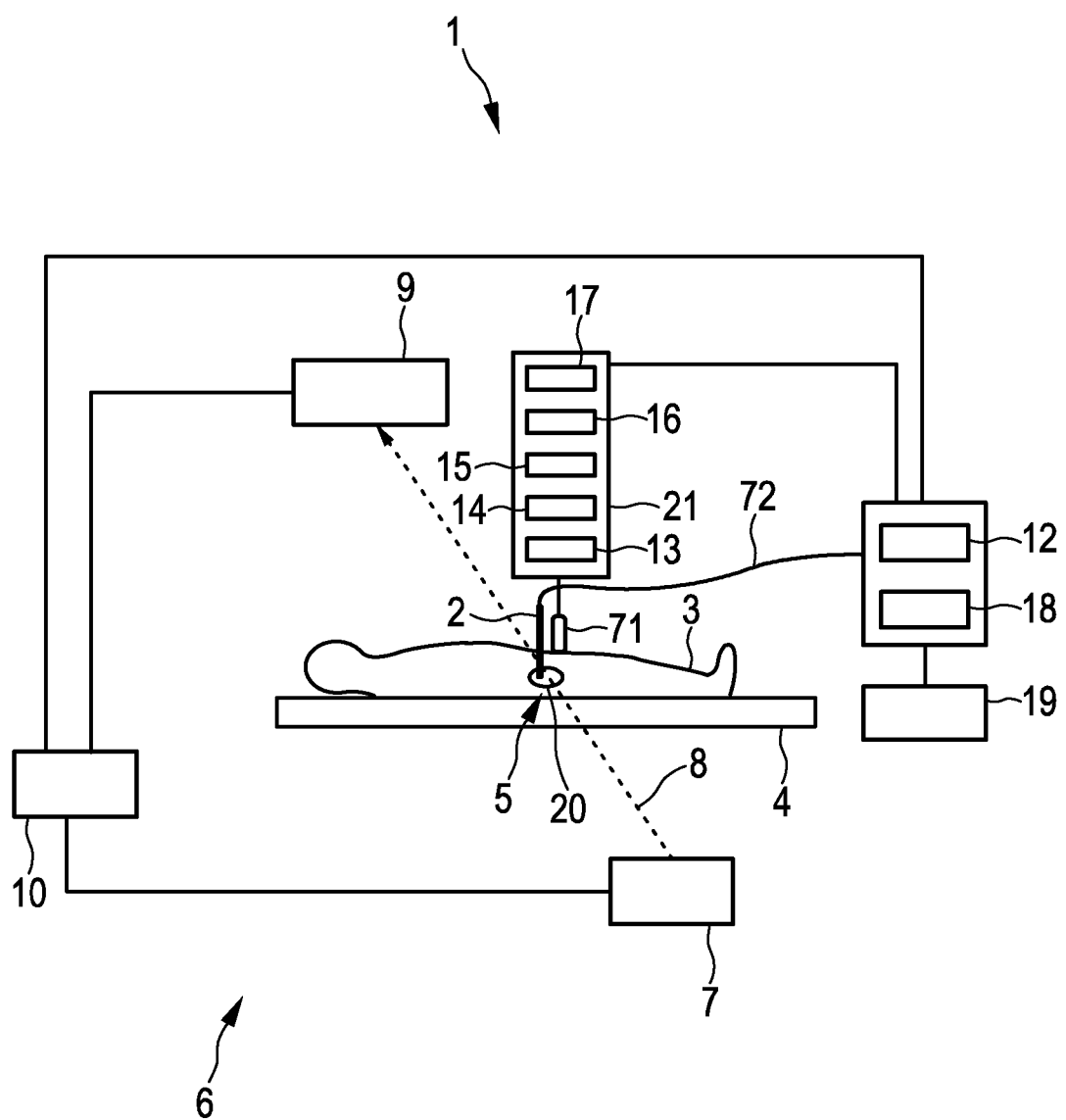
FIG. 1 shows schematically and exemplarily an embodiment of a system for applying energy to an object.

FIG. 1 shows schematically and exemplarily an embodiment of a system for applying energy to an object. In this embodiment the system is an ablation system for ablating a tumor within a person 3 lying on a support means 4 like a patient table. The system 1 comprises an energy application element for applying energy to a person 3, in particular, to a tumor within the person 3. In this embodiment the energy application element 2 is an ablation needle comprising ablation electrodes and temperature sensing elements at the tip 5 of the ablation needle 2. The temperature sensing elements at the tip 5 of the ablation needle 2 are preferentially thermocouples, which are electrically connected to a tip temperature measurement determining unit 18 for determining the temperature at the tip 5 of the ablation catheter 2 depending on electrical signals received from the thermocouples.

The energy applied to the person 3 by the ablation electrodes is preferentially RF energy, wherein the ablation electrodes are electrically connected to an ablation energy control unit 12 for controlling the application of the RF energy via an electrical connection 72. In this embodiment the ablation energy control unit 12 comprises an RF source for providing the RF energy.

Figure 2:
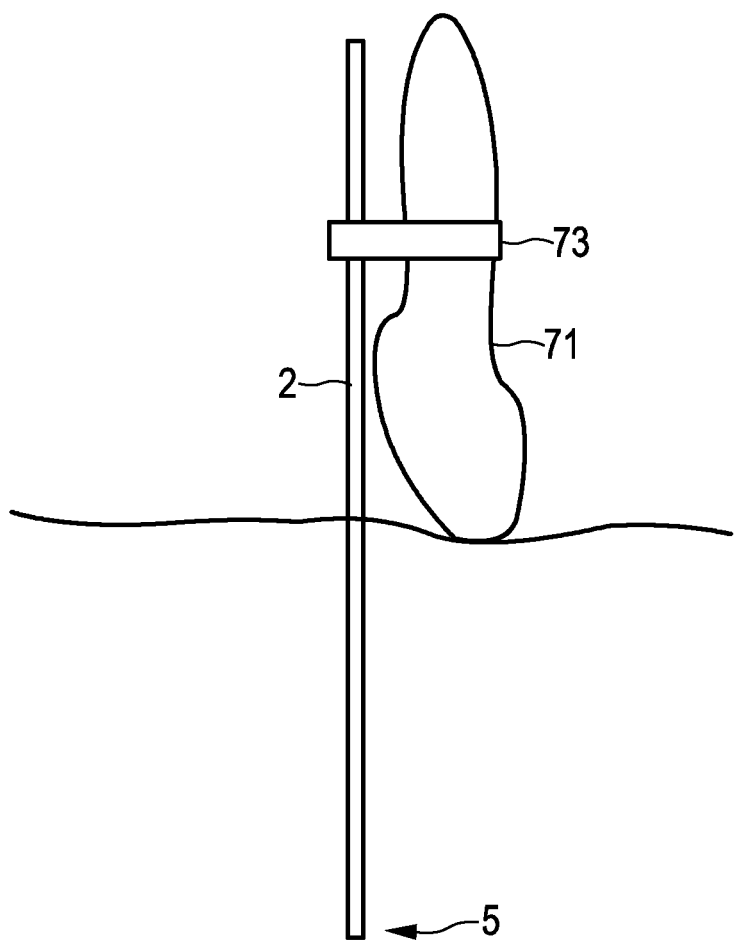
FIG. 2 shows schematically and exemplarily an arrangement of an ultrasound probe, an ablation needle and a fixture.

The system 1 further comprises a temperature distribution measuring unit for measuring a spatially and temporally dependent first temperature distribution in a first region within the person 3 within a first temperature range, while the RF energy is applied to the person 3. The temperature distribution measuring unit comprises an ultrasound probe 71 for acquiring ultrasound data of the first region and an ultrasound thermometry unit 13 for determining the first temperature distribution based on the acquired ultrasound data. In this embodiment the ultrasound probe 71 is adapted to acquire the ultrasound data in two planes being orthogonal to each other and defining the first region. However, in another embodiment the ultrasound probe can be adapted to acquire ultrasound data in other planes defining the first region, wherein the ultrasound probe may be a volume ultrasound probe. The ultrasound probe 71 may be fixed to the ablation needle 2 by using a fixture 73 such that the first temperature distribution in the first region is measurable by ultrasound thermometry. A preferred arrangement of the ablation needle 2, the ultrasound probe 71 and the fixture 73 is schematically and exemplarily shown in FIG. 2.

The system 1 further comprises a model providing unit 14 for providing a model describing a model temperature distribution in the first region and in a second region within the person 3 depending on modifiable model parameters, wherein the second region is closer to the tip 5 of the ablation needle 2 than the first region. The modifiable parameters include thermal parameters like the thermal conductivity and electrical parameters like the electrical conductivity of the liver 20.

The system 1 also comprises a temperature distribution estimating unit 15 for estimating a spatially and temporally dependent second temperature distribution in the second region within a second temperature range, which is different to the first temperature range and in which the temperature distribution measuring unit 13, 71 cannot measure a temperature distribution, while the energy is applied to the person 3, by modifying the model parameters such that a deviation of the model temperature distribution from the first temperature distribution in the first region and from the temperature measured by the thermocouples at the tip 5 of the ablation needle 2 is minimized. At the beginning of the minimization process the provided model can be initialized by using initial model parameters, which are person-specific. For example, the ultrasound probe 71 and ultrasound thermometry unit 13 can be adapted to measure the velocity of blood flowing through a vessel within the person based on a Doppler ultrasound technique, wherein this measurement can be performed before the person 3 is heated by applying the ablation energy. However, the second temperature distribution in the second temperature range can also be determined, without performing this prior ultrasound measurement, wherein in this case, for instance, already known model parameters like model parameters known from literature can be used as initial model parameters, which are then modified during the minimization process.

The first region has a distance to the tip 5 of the ablation needle 2 such that the temperature in the first region will be smaller than about 50 degrees Celsius, if the ablation energy is applied to the person 3. This ensures that the temperature distribution measuring unit 13, 71 can measure the first temperature distribution also during the ablation procedure. The second region is closer to the tip 5 of the ablation needle 2. Preferentially, the second region is adjacent to the tip 5 of the ablation needle 2 and covers a region of interest to be ablated and a surrounding region surrounding the region of interest. In this embodiment the region of interest is a tumor region within the liver 20. Thus, the ultrasound thermometry unit 13, the model providing unit 14 and the temperature distribution estimating unit 15 are preferentially adapted such that the temperature distribution can be estimated in the tumor region and in a surrounding region around the tumor region, wherein these regions may define the second region and wherein the second temperature distribution is the temperature distribution estimated in this second region. The second temperature region can also be a larger region, which also covers further regions, which are further away from the tip 5 of the ablation needle 2 and in which the tissue is also heated to a temperature larger than 50 degrees Celsius.

The temperature distribution measurement unit 13, 71, the model providing unit 14 and the temperature distribution estimating unit 15 form a temperature distribution determining apparatus 21 for determining an overall temperature distribution within the person 3 covering the first and second temperature distributions.

The temperature distribution determining apparatus 21 comprises an ablated region determining unit 16 for determining an ablated region defining a region within the object that has been ablated, wherein the ablated region determining unit 16 is adapted to determine the ablated region by determining a part of the person 3 for which the estimated second temperature distribution comprises or has comprised a temperature being larger than a predefined temperature threshold. The temperature distribution determining apparatus 21 also comprises a region of interest providing unit 17 for providing the region of interest being, in this embodiment, a tumor region, which should be ablated, wherein the determined ablated region and the tumor region can be shown on a display 19. For instance, an overlay of the determined ablated region and the tumor region can be shown on the display 19. The predefined temperature threshold is, for instance, 60, 65 or 70 degrees Celsius.

The ablation energy control unit 12 can be adapted to control the ablation needle 2, i.e. the power of the ablation, depending on the determined temperature distribution. In particular, the ablation energy control unit 12 can be adapted to control the ablation power such that the tumor region is completely ablated.

Referring again to FIG. 1, the system 1 comprises a position detection system 6 for detecting the position of the tip 5 of the ablation needle 2 within the person 3. In this embodiment the position detection system 6 is an x-ray fluoroscopy system, in particular, an x-ray C-arm system. The x-ray fluoroscopy system comprises an x-ray source 7 for generating x-rays 8 which traverse the person 3 on the table 4, wherein the x-rays 8, which have traversed the person 3, are detected by an x-ray detector 9. The x-ray fluoroscopy system 6 further comprises a fluoroscopy control unit 10 for controlling the x-ray source 7 and the x-ray detector 9. The x-ray detector 9 generates x-ray images of the person 3, which can be shown on the display 19. On the generated x-ray images the tip 5 of the ablation needle 2 is visible within the person 3 such that the x-ray images show the position of the tip 5 of the ablation needle 2 within the person 3. In other embodiments other position detection systems for detecting the position of the needle tip within the person can be used like position detection systems which are based on electromagnetic sensors, ultrasound sensors, et cetera.

In this embodiment the ablation needle 2 is navigated directly by hand. In another embodiment the system can further comprise a navigation unit for navigating the ablation needle, in particular the needle tip, to a desired location within the person. The navigation unit can be adapted to allow a user to navigate the ablation needle completely by hand or semi-automatically. The ablation needle may comprise built-in guiding means, which can be controlled by the navigation unit. The ablation needle can, for example, be steered and navigated by the use of steering wires, in order to guide the needle tip to a desired location within the person.

Thermal ablation techniques are excellent alternatives to major surgery, which can pose a risk even with the most experienced surgeon. These techniques are minimally invasive requiring only needles, which may be adapted to perform an RF therapy, a cryotherapy or a microwave ablation therapy, or they are non-invasive, wherein, for instance, a non-invasive heat source such as an ultrasound heating source like a high intensity focused ultrasound (HIFU) source is used. In most of the procedures, cancerous tissue is heated to temperatures above 60 degrees Celsius and coagulated.

For performing an RF ablation (RFA) procedure the system described above with reference to FIG. 1 comprises a probe with an active electrode tip, i.e. the ablation needle, through which preferentially a 460 to 500 kHz alternating current is conducted. The current propagates through the body of the person 3 to grounding pads (not shown in FIG. 1 for clarity reasons) placed either on the back or the thigh of the person 3. The current causes ionic agitation and frictional heating. Heat is then dissipated through thermal conduction to ablate the tumor region. In this embodiment RFA is used to treat liver cancer.

In the embodiment described above with reference to FIG. 1 RFA is performed under x-ray guidance by using an x-ray C-arm system. However, the RFA can also be performed by using another guidance system, which may be based on ultrasound imaging, computed tomography (CT) imaging or magnetic resonance imaging (MRI) guidance. A follow-up examination is preferentially done by using a CT scan or MRI scan within, for example, a month to assess effectiveness of ablation and again at three month intervals along with tumor markers to detect residual disease or recurrence. After state of the art ablation procedures have been performed, relatively high recurrence rates are often observed because of the often present inability to monitor and control ablation size sufficiently to adequately kill the tumor cells. The system described above with reference to FIG. 1 provides therefore real-time feedback to the clinician by providing a temperature map of the ablated zone. This could also be achieved with reasonable accuracy with MR based temperature imaging. However, MRI is expensive and may not be readily available. Ultrasound is another modality that may be used for image guidance during placement of the needle. Due to its ease of use and availability it may be a preferred method for monitoring the lesions. However, in the prior art ultrasound is used generally for monitoring the treatment by visualizing the hyperechoic lesions on a B-mode image. Such visualization is only approximate and not a good indicator of the treatment efficacy.

The system described above with reference to FIG. 1 uses an ultrasound probe 71 and an ultrasound thermometry unit 13 for performing three-dimensional ultrasound thermometry. The ultrasound probe 71 and the ultrasound thermometry unit 13 are adapted to determine the three-dimensional spatial and temporal first temperature distribution as described, for instance, in the article "Three-dimensional spatial and temporal temperature imaging in gel phantoms using backscattered ultrasound" by A. Anand et al., IEEE Transactions on Ultrasonics, Ferroelectrics and Frequency Control, 54(1), pages 23 to 31 (2007), which is herewith incorporated by reference.

The underlying principle of ultrasound thermometry is that the speed of sound in tissue changes as a function of temperature which manifests as apparent shifts, i.e. displacements, in ultrasound echoes. The resulting "temperature-induced strain", which is mathematically derived by differentiating the displacement along the ultrasound beam direction, is nominally proportional to the temperature rise in the range up to 50 degrees Celsius. However, the problem lies in the variation in trend of the temperature dependence of speed of sound for various tissues. For example, for liver tissues the speed of sound increases approximately linearly with temperature up to a temperature range of 50 degrees Celsius, after which the trend plateaus. Hence, there is no sensitivity to ultrasound echo shifts with temperatures beyond this temperature range. Also, with the onset of tissue necrosis and the resulting changes in tissue structure, the signature of the ultrasound echoes changes significantly and makes the comparison of ultrasound echoes to determine the displacement difficult. Therefore, for temperatures above 50 degrees Celsius the ultrasound thermometry, which is based on tracking changes in speed of sound, is not a reliable indicator of temperature in the tissue. In this embodiment the first temperature range is therefore defined by an upper border being about 50 degrees Celsius. A lower border of the first temperature range may be defined by the normal temperature of the person, i.e. by 37 degrees Celsius. The ultrasound thermometry unit 13 is adapted to ultrasonically measure the first temperature distribution in this first temperature range.

The temperature distribution determining apparatus 21 is adapted to i) measure ultrasound echo shifts away from the core of the heating zone, where the temperature is less than 50 degrees Celsius, i.e. in the first region, ii) couple these echo shifts to the thermal model and iii) use the thermal model to infer temperatures over a larger volume including the core of the heating zone, i.e. including the second region. The temperature distribution determining apparatus 21 is designed so that it is not necessary to perform a test shot, i.e. it is not necessary to perform the ultrasound thermometry procedure before applying the ablation energy. The relevant parameters needed by the model are estimated during the ablative treatment itself. The goal of this approach is to provide the physician with an estimated temperature map, which also covers the ablation zone.

The temperature distribution determining apparatus 21 is adapted to use ultrasound thermometry to continuously monitor the temperature at a spatial location away from the ablation or high temperature zone and consequently estimate the temperature in the ablation zone with a thermal model based approach. By using this approach the temperature distribution determining apparatus 21 may solve following problems of the prior art.

The extent of an ablated region may be determined more accurately. Moreover, in the prior art ultrasound B-mode inspection guided by hyperechoic visualization of the ablated region is often not accurate, which may render it difficult to assess the effectiveness of therapy. The hyperechoes visualized on B-mode images are caused by gas and vapor bubbles. In order to generate these bubbles and visualize the treatment region on ultrasound, an ablation treatment protocol involves heating to temperatures in the order of 100 degrees Celsius which is overkill for achieving necrosis that only requires temperatures up to 70 to 80 degrees Celsius. Hence, if ultrasound B-mode imaging is used for visually monitoring the ablation procedure, the treatment time is longer than it needs to be. Furthermore, known ultrasound thermometry techniques cannot be used in monitoring the ablated region, when it has a temperature exceeding about 50 degrees Celsius. In addition, bubbles released in the treatment region may it make difficult to reliably use ultrasound.

The temperature distribution determining apparatus overcomes these drawbacks by providing a completely different approach, wherein the temperature in the ablation zone is estimated as described above by using i) a thermal model and ii) the temperature measured at a spatial location away from the ablation zone. Furthermore, this can improve the effectiveness of readily available ultrasound during RF ablation treatments and provide instant feedback on the treatment. Moreover, since no "test" shot is necessarily required as in EP 2 387 963 A1, the treatment time can be optimized, which may result in improved patient throughput.

The temperature distribution determining apparatus 21 is adapted to utilize ultrasound thermometry for measuring temperatures at a location away from the ablated (high-temperature) zone, i.e. for measuring the first temperature distribution in the first region. Subsequently, the evolution of the three-dimensional first temperature distribution is used in conjunction with a thermal model based approach to predict temperature rise in the ablation zone, i.e. to predict the second temperature distribution in the second region. In this treatment regimen, the robustness of thermal strain derived temperature data obtained at a low-temperature region is utilized for accurate prediction of temperatures in the tumor margin where the ablative therapy is to be performed. By following the above procedure, ultrasound data is obtained away from the bubbles released during the procedure, wherein the ultrasound data are acquired for regions with a low to moderate increase in temperatures, i.e. for regions within a first absolute temperature range of about 37 to 50 degrees Celsius. In addition, the thermal model preferentially takes into account the local temperature dependence on tissue properties and blood vessel perfusion to provide an accurate temperature map in the ablated region.

Figure 3:
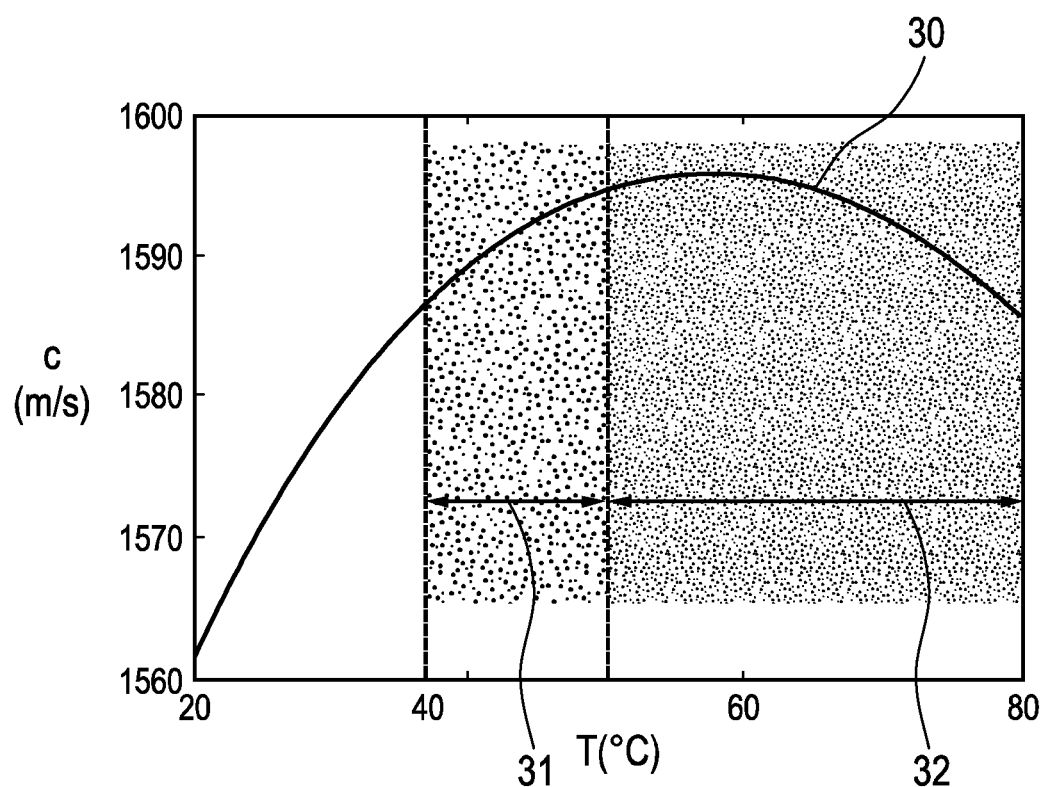
FIG. 3 shows a diagram illustrating a first temperature range, in which ultrasound thermometry can be performed, and a second temperature range, in which ultrasound thermometry cannot be performed, FIG. 4 exemplarily shows a block diagram illustrating an embodiment of a temperature distribution determining method for determining a temperature distribution within an object caused by applying energy to the object, FIG. 5 schematically and exemplarily shows a temperature distribution around a tip of an ablation needle and ultrasound monitoring planes defining a first region, in which ultrasound thermometry is performed.

The diagram shown in FIG. 3 exemplarily illustrates the first and second temperature ranges, wherein the temperature distribution measuring unit 13, 71 measures the first temperature distribution in the first temperature range 31 and wherein the temperature distribution estimating unit 15 estimates the second temperature distribution in the second temperature range 32. As can be seen in FIG. 3, the ultrasound-velocity-c-versus-temperature-T curve 30 plateaus around 50 degrees Celsius. The ultrasound thermometry data provided by the temperature distribution measuring unit 13, 71 are therefore only valid below 50 degrees Celsius, wherein for larger temperatures, i.e. in the second temperature range 32, the thermal model approach is used.

In the following an embodiment of a temperature distribution determining method for determining a temperature distribution within an object caused by applying energy to the object will exemplarily be described with reference to a block diagram shown in FIG. 4.

Figure 4:
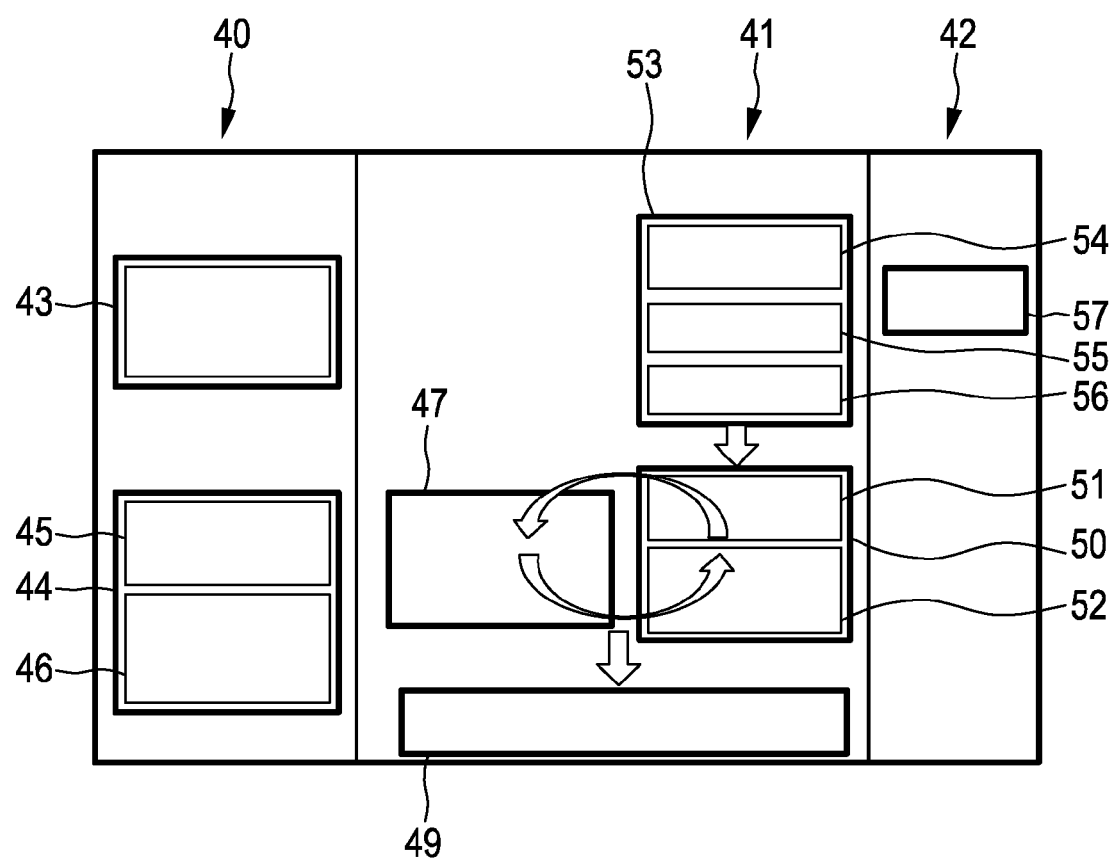

In the block diagram shown in FIG. 4 three phases are illustrated, a pre-treatment phase 40, a treatment phase 41 during which the RF ablation energy is applied, and a post-treatment phase 42.

Figure 5:
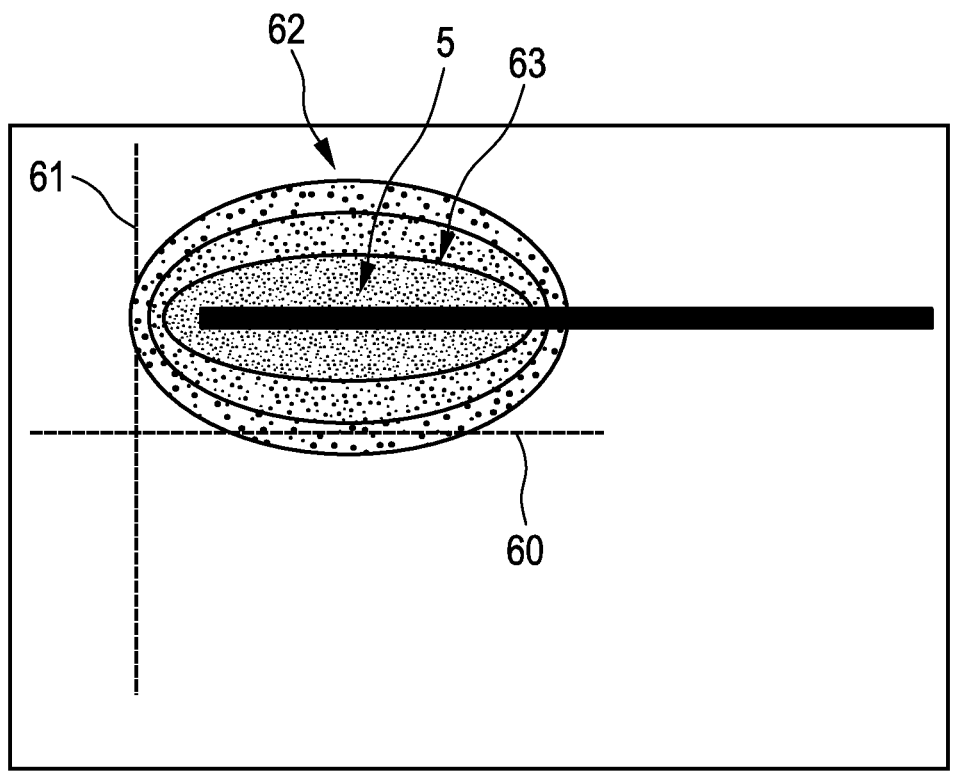

In the pre-treatment phase 40 the ablation needle 2, in particular, the tip 5 of the ablation needle 2, is inserted into the liver 20 of the person 3 and the ultrasound probe 71 is arranged such that the first temperature distribution can be measured in ultrasound monitoring planes placed at spatial locations far enough from the ablation zone, where the temperature during the application of the RF ablation energy is expected to be less than 50 degrees Celsius (box 43 in FIG. 4). The ultrasound monitoring planes define the first region, in which the first temperature distribution will be measured during the application of the RF ablation energy. The ultrasound probe 71 can be a matrix ultrasound probe that can be arranged such that a first ultrasound monitoring plane is parallel to the tip 5 of the ablation needle 2 and that a second ultrasound monitoring plane is perpendicular to the tip 5 of the ablation needle 2. FIG. 5 schematically and exemplarily illustrates a possible arrangement of the ultrasound monitoring planes.

In FIG. 5 the ultrasound monitoring planes 60, 61 are perpendicular to each other, wherein a first ultrasound monitoring plane is parallel to the tip 5 of the ablation needle 2 and a second ultrasound monitoring plane 61 is perpendicular to the tip 5 of the ablation needle 2. FIG. 5 further indicates a temperature distribution 62 around the tip 5 of the ablation needle 2 during the application of the RF ablation energy, wherein in a region 63 close to the tip 5 of the ablation needle 2 the temperature is very high such that the liver tissue is ablated in this region, i.e. the region 63 is an ablated region.

By placing the ultrasound monitoring planes 60, 61 away from the region around the tip 5 of the ablation needle 2, in which the liver tissue will be ablated, it can be ensured that the temperature rise in these ultrasound monitoring planes 60, 61 and, thus, in the first region defined by these ultrasound monitoring planes 60, 61 is slow and the absolute temperature is below 50 degrees Celsius. Additionally, this placement of the ultrasound monitoring planes 60, 61 can ensure that ultrasound backscatter echoes measured by the temperature distribution measuring unit 13 produce reliable shifts, without any corruption of the ultrasound data from any hyper echoes resulting from bubbles or resulting from the tip 5 of the ablation needle 2.

The placement of the ultrasound probe 71 can be done with help of a fixture coupled to the ablation needle that holds the ultrasound probe 71 at a given distance of, for instance, 2 cm away from the tip 5 of the ablation needle 2. This distance between the ultrasound probe and the ablation needle is preferentially a distance in a direction being perpendicular to the ablation needle 2 and parallel to the fixture 73 in the configuration schematically and exemplarily shown in FIG. 2. In the pre-treatment phase 40 the ultrasound probe 71 or another ultrasound probe can be used to identify possible needle paths for insertion into the tumor and to place the ultrasound monitoring planes for the ultrasound thermometry as desired.

Moreover, in the pre-treatment phase 40 the model providing unit 14 provides a thermal model for describing a model temperature distribution in the first region, in particular, in the ultrasound monitoring plane 60, 61 and in a second region, in particular, in the region adjacent to the tip 5 of the ablation needle 2 during the application of the RF ablation energy. For providing this model the model providing unit 14 uses medical images of the liver 20 including the tumor region like CT images or MR images. The tumor and other structures like blood vessels are identified and segmented in the medical images and this information is used together with initial model parameter values for providing an initialized thermal model. For instance, thermal and electrical parameters of the different identified and segmented structures can be initially provided for providing an initial thermal model. The initial model parameters can be tissue properties like the thermal conductivity and the electrical conductivity of different kinds of tissue or other parameters like perfusion parameters, directional flow parameters, parameters of the tip of the ablation needle, et cetera. Perfusion parameters and directional flow parameters may be initially determined by using already known information, which may be known from other measurements, which have been performed before. For instance, an ultrasound Doppler measurement can be performed, in order to determine typical flow velocities and, thus, directional flow parameters and perfusion parameters. In FIG. 4 the provision of the initialized model is indicated by the box 44, wherein the box 45 indicates the identification and segmentation of structures within the liver and the box 46 indicates the provision of the model parameters like tissue properties. In an embodiment the initial model has already been determined and initialized in advance and just needs to be loaded from the model providing unit 14 in the pre-treatment phase 40.

The thermal model is preferentially a finite element implementation of the bioheat transfer equation (BHTE) proposed by H. H. Pennes, for example, in the article "Analysis of tissue and arterial blood temperatures in the resting human forearm", 85:5-34, Journal of Applied Physiology (1998), which is herewith incorporated by reference.

The bioheat transfer equation models thermal diffusion and perfusion in tissue. It includes a modeling of the RFA heat source, wherein a Laplace equation is implemented. The model considers directional flow in large blood vessels by using equations for heat transfer in fluids. In the case of a model for liver tissue initial model parameters are, for instance, an electrical conductivity of 0.148 S/m, a thermal conductivity of 0.465 W/mC, a density of 1060 kg/m$^3$, a heat capacity of 3600 J/Ckg and a perfusion rate of $6.4 \times 10^{-3}$/s. Further initial model parameters can be properties of the ablation needle as documented by the respective manufacturer, in order to consider an influence of the ablation needle properties on the electrical current distribution and the heat transfer.

During the treatment phase 41 the ultrasound thermometry is performed as indicated by the box 53. The ultrasound probe 71 performs, for instance, a three-dimensional ultrasound backscatter acquisition procedure, wherein optionally a respiratory gating can be performed. This is indicated by the box 54. The ultrasound thermometry unit 13 estimates then ultrasound echo shifts from the acquired three-dimensional ultrasound backscatter data as indicated by the box 55, whereupon the thermal strain and finally the temperature is estimated by the ultrasound thermometry unit 13 as indicated by the box 56.

In this embodiment the ultrasound thermometry 53 is performed such that the first temperature distribution in the ultrasound monitoring planes 60, 61 can be measured during the treatment phase 41, i.e. during the application of the RF ablation energy to the tumor region. Thus, during the treatment the ultrasound echoes are analyzed for apparent displacements as a result of the heating, wherein these displacements, which can also be regarded as shifts, are converted to thermal strain values and finally to the temperature and wherein for determining the temperature depending on the thermal strain values known assignments between thermal strain values and temperatures can be used, which can be predetermined by calibration measurements.

The box 50 indicates an updating of the model parameters based on the measured first temperature distribution and based on an actual estimated second temperature distribution obtained from running the thermal model. The estimation of the second temperature distribution by running the thermal model is indicated by the box 47.

During the ultrasound thermometry procedure, i.e. in parallel, the thermal model is executed with the initialized parameters, thereby generating an actual spatial temperature estimation, which is compared with the first temperature distribution obtained from the ultrasound thermometry procedure 53. The comparison of these model estimates with the result of the ultrasound thermometry procedure 53 is indicated by the box 51. Using this comparison, the model parameters are constantly updated using established minimization methods to minimize the difference between the model prediction and the ultrasound experimental data. This modification of the model parameters is indicated by the box 52. The model parameters, which are optimized in this way, include, for instance, thermal constants such as the thermal diffusivity, electrical properties such as the electrical conductivity, properties of heat sinks caused by perfusion, convective cooling due to blood flow, et cetera. This optimization process provides flexibility in the model, which allows accounting for local heterogeneities that are to be expected in biological tissue.

For executing the model known multi-physics simulation tools like COMSOL can be used, which combine electrical heat generation and the subsequent heat transfer in the medium. Heat sinks are large blood vessels in the vicinity of the ablation zone. They can be characterized by the flow rate, the flow direction and the location and size of these vessels with respect to the energy application element. These properties can be incorporated in the bioheat transfer equation, and these properties and further properties of the model can be optimized such that a deviation between the model temperature distribution and the measured first temperature distribution is minimized.

As the model parameters are optimized, a temperature map is generated and updated in a region of interest being preferentially a treatment region of interest covering the tumor. The temperature map can be used to generate an ablation contour by defining the region within the liver 20, which is or has been heated to a temperature being larger than a predefined temperature threshold. This generation of the temperature map and the optional determination of the ablation contour are indicated by the box 49. The region of interest can be regarded as being the second region, in which the second temperature distribution is estimated, or the second region can be a larger region that covers at least the region of interest with the tumor. During the entire process in the treatment phase 41 the ultrasound echo shifts are constantly analyzed in the region away from the ablation zone, i.e. in the first region defined by the ultrasound monitoring planes 60, 61 in this embodiment, such that there is a realistic feedback to the model that takes into account, for instance, the tissue properties and the perfusion effects on the spatial-temporal distribution of the heat.

For updating the model parameters in the treatment phase 41 not only the temperature distribution in the ultrasound monitoring planes 60, 61 may be compared with the estimated temperature distribution obtained from the thermal model, but additionally also a temperature at the tip of the ablation needle as measured by, for instance, thermocouples may be compared with the estimated temperature distribution obtained from the thermal model, wherein the model parameters can be optimized such that the estimated temperature distribution fits as good as possible to the temperature distribution in the ultrasound monitoring planes measured by ultrasound thermometry and the temperature measured by the thermocouples at the tip of the ablation catheter.

The temperature map can be used as a feedback to control a power output of the ablation energy control unit 12 controlling the application of the RF ablation energy.

In the post-treatment phase 42 the temperature map and/or the ablation contour may be shown overlaid on the region of interest, in particular, overlaid on the tumor region, to get a realistic sense of the effectiveness of the treatment. It may then be decided based on this overlay image, whether an additional treatment is necessary. This is indicated by the box 57.

Figure 6:
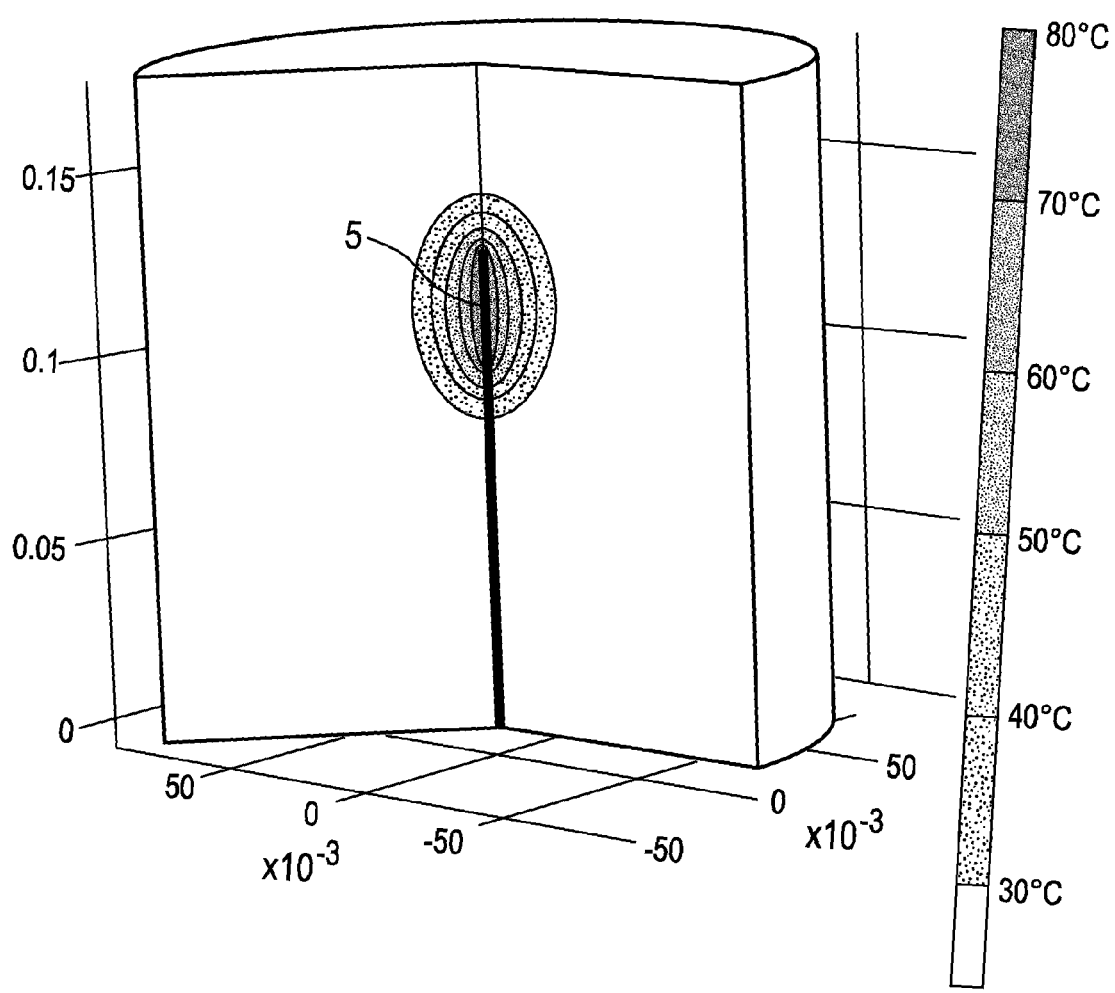
FIG. 6 shows a further temperature distribution around a tip of an ablation needle.

FIG. 6 shows schematically and exemplarily a three-dimensional temperature distribution as defined by an optimized thermal model, which has been optimized by minimizing differences between estimated temperature values and measured temperature values in accordance with the embodiment described above with reference to FIG. 4.

Figure 7:
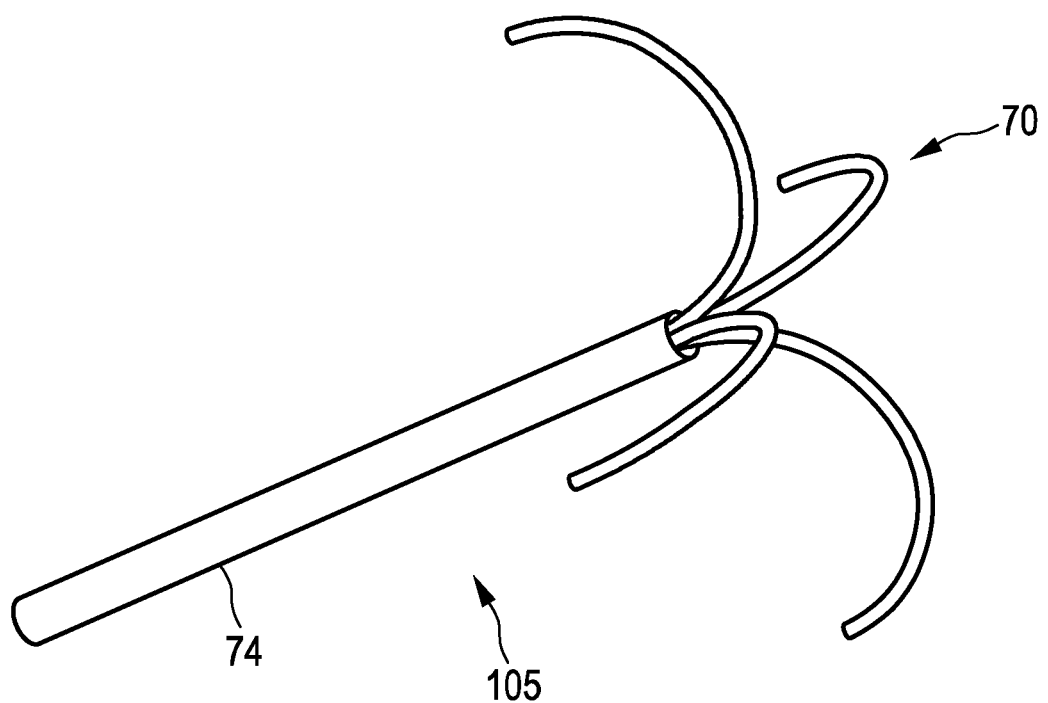
FIG. 7 shows schematically and exemplarily an embodiment of a tip of an ablation needle, FIG. 8 schematically and exemplarily illustrates several first regions having different distances to an ablation needle.

The tip of the ablation needle can comprise a substantially straight ablation electrode and optionally also temperature sensing elements like thermocouples. However, the tip of the ablation needle can also comprise another arrangement of one or several ablation electrodes, which may or which may not comprise temperature sensing elements like thermocouples. For instance, as schematically and exemplarily shown in FIG. 7, the tip 105 of the ablation needle can comprise several ablation electrodes 70 with integrated thermocouples, wherein the ablation electrodes 70 with the integrated thermocouples are retractable into a shaft 74 of the ablation needle.

In a further embodiment the temperature measuring unit 13, 71 is adapted such that the first region is modified depending on the measured first temperature distribution, in order to measure different first temperature distributions in different first regions. In particular, the temperature distribution measuring unit is adapted such that the first region is modified by changing the position of the first region. The first region is formed by a plane, wherein the temperature distribution measuring unit is preferentially adapted such that the planar first regions are consecutively located at different positions, wherein, if the position of the first region is changed, it is changed from a position being closer to the ablation needle 2 to a position being more distant to the ablation needle 2.

The temperature distribution measuring unit, in particular, the ultrasound thermometry unit 13, can comprise a storing unit, in which a sequence of predefined positions is stored, wherein during the actual measurement this stored predefined sequence can be used for positioning the planar first region. The different positions can be equidistant such that it is just required to store a single distance value and a direction for defining the sequence of positions. However, the sequence of positions can also comprise non-equidistant positions such that the positions may be stored by storing a sequence of distance values, which are at least partly different, and a direction. The sequence of positions can be predefined based on calibration measurements or it can be manually predefined by a user as desired. The sequence of positions can also be predetermined by thermal modeling using a database of typical tissue electrical and thermal properties and organ-specific characteristics. Based on the thermal model the positions with relatively high thermal gradients can be identified and these positions can be avoided, wherein also positions with relatively low thermal gradients can be identified and used for defining the positions of the scan planes. Thus, based on the thermal model thermal gradients can be determined and the sequence of positions may be determined by thresholding the thermal gradients. The thermal gradients used for predetermining the sequence of positions are preferentially spatial gradients.

In an embodiment the predetermination of the sequence of positions may also include the expected temperature rise at the respective position, wherein a position at which the temperature will expectedly rise up to 50 degrees Celsius is preferred in comparison to a position at which the temperature will expectedly not rise to such a high temperature during the modelled heating process. For instance, for each position a selection factor may be calculated being a combination, in particular, a linear combination, of a first value being indicative of the expected temperature rise at the respective position and a second value being indicative of the expected temperature gradient at this position during the modelled heating process, wherein the sequence of positions can be predetermined based on the calculated selection factors. Preferentially, the first value increases with an increasing expected temperature rise and the second value increases with a decreasing expected temperature gradient. The temperature gradient used for the determination of the positions is preferentially the highest spatial temperature gradient to be expected at the respective position during the modelled heating process. For modelling the heating process known bioheat transfer models can be used as the thermal model, which may be implemented by using multi-physics finite elements tools such as COMSOL. Different positions of the planar first regions, i.e. of the different ultrasound scan planes, are schematically and exemplarily illustrated in FIG. 8.

Figure 8:
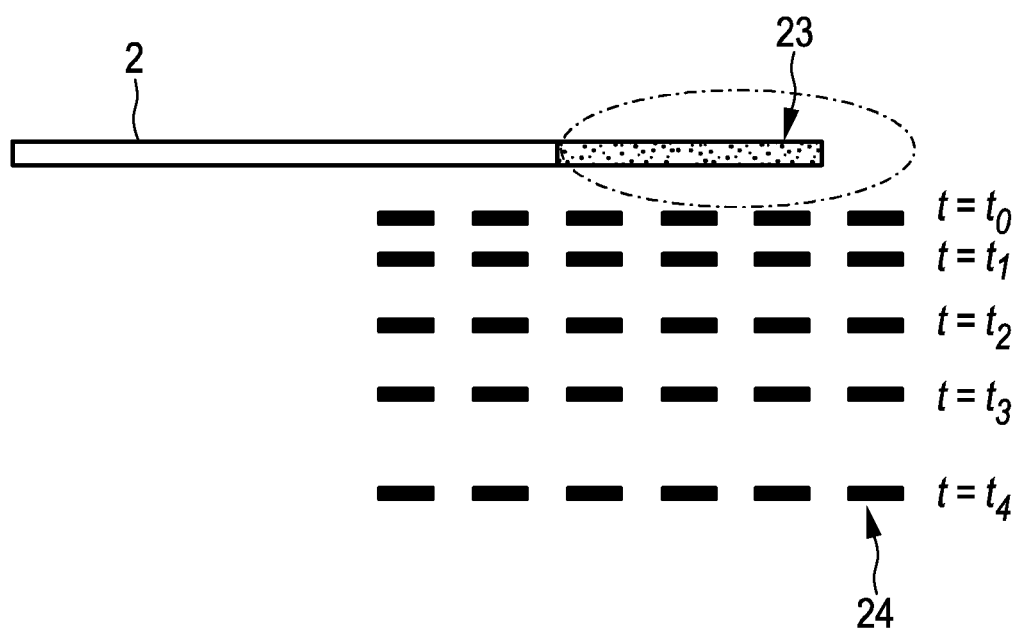

FIG. 8 shows the ablation needle 2 with a heating region 23 formed by ablation electrodes (not shown) located in the heating region 23. The temperature distribution measuring unit 13, 71 is adapted such that the different first regions correspond to different distances of the ultrasound scan plane to the ablation needle 2. The corresponding different first regions 24 are indicated in FIG. 8 by broken lines. At an initial time $t_0$ the first temperature distribution is measured in a first region being relatively close to the ablation needle 2. When the measured first temperature distribution in the current first region at the time $t_0$ includes a temperature outside of a predefined temperature range being preferentially a temperature range having a maximum temperature of 50 degrees Celsius, the temperature distribution measuring unit 13, 71 modifies the first region for measuring the first temperature distribution in a further first region by changing the position of the first region. In FIG. 3 the further first region corresponds to the ultrasound scan plane at the time $t_1$. The temperature distribution measuring unit then measures the temperature distribution in this further first region and, when the measured temperature distribution includes a temperature being outside of the predefined temperature range, the temperature distribution measuring unit 13, 71 measures the temperature distribution in an even further first region indicated in FIG. 3 by the ultrasound scan plane at the time $t_2$. This moving from first region to first region, in particular, from ultrasound scan plane to ultrasound scan plane, is continued with further, more distant first regions like the first regions indicated in FIG. 8 by the broken lines at the times $t_3$ and $t_4$.

In this embodiment the ultrasound probe 71 comprises a two-dimensional ultrasound transducer for acquiring the ultrasound data of the different first regions, i.e. in this embodiment of the different ultrasound scan planes. This allows acquiring the ultrasound data of the different first regions without mechanically moving the ultrasound probe 71. In another embodiment the ultrasound probe can comprise a one-dimensional ultrasound transducer, wherein in this case the one-dimensional ultrasound transducer is mechanically movable with respect to the ablation needle 2, in order to acquire ultrasound data of the different first regions having the different distances to the ablation needle.

The temperature distribution measuring unit 13, 71 is adapted such that the ultrasound probe 71 acquires reference ultrasound data of the different first regions 24 at reference temperatures and actual ultrasound data of the different first regions 24 and that the ultrasound thermometry unit 13 determines the first temperature distribution in the respective first region 24, i.e. in the ultrasound scan plane having the respective distance to the ablation needle 2, depending on respective actual ultrasound data acquired for the respective first region 24, the reference ultrasound data acquired for the respective first region 24 and the respective reference temperature. In particular, the ultrasound thermometry unit 13 is preferentially adapted to determine a three-dimensional spatial and temporal temperature distribution in the respective first region 24 for the time period in which ultrasound data have been acquired for the respective first region 24 as described, for instance, in the above mentioned article by A. Anand et al., which is herewith incorporated by reference.

In this embodiment the temperature distribution measuring unit 13, 71 is adapted such that in a reference data acquisition stage the ultrasound probe 71 acquires the reference ultrasound data for the different first regions 24 at a known reference temperature being, in this embodiment, 37 degrees Celsius and that in a temperature distribution measurement stage the ultrasound probe 71 acquires actual ultrasound data and the ultrasound thermometry unit 13 determines the first temperature distributions in the different first regions 24 depending on respective actual ultrasound data acquired for the respective first region 24, the reference ultrasound data acquired for the respective first region 24 and the known reference temperature.

Moreover, in this embodiment the model providing unit 14 may be adapted to provide the model such that it describes a model temperature distribution in the different first regions and in the second region within the object depending on the modifiable parameters and wherein the temperature distribution estimating unit 15 is adapted to estimate the second temperature distribution in the second region within the second temperature range, while the energy is applied to the object, by modifying the model parameters such that a deviation of the model temperature distribution from the measured first temperature distributions in the first regions is minimized. In particular, the model providing unit 14 is adapted to provide a model of the object describing a model temperature distribution in the first regions 24 for time periods, in which the respective first temperature distribution has been measured in the respective first region, and for time periods, in which the respective first temperature distribution has not been measured in the respective first region 24, and in the second region, wherein the temperature distribution estimating unit 15 is adapted to estimate spatially and temporally dependent temperature distributions in the different first regions for time periods, in which the respective first temperature distribution has not been measured in the respective first region 24, and in the second region by modifying the model parameters such that a deviation of the model temperature distribution in the different first regions 24 for the time periods, in which the respective first temperature distribution has been measured in the respective first region 24, from the measured temperature distributions in the different first regions 24 is minimized and by determining the estimated temperature distributions from the modified model.

Figure 9:
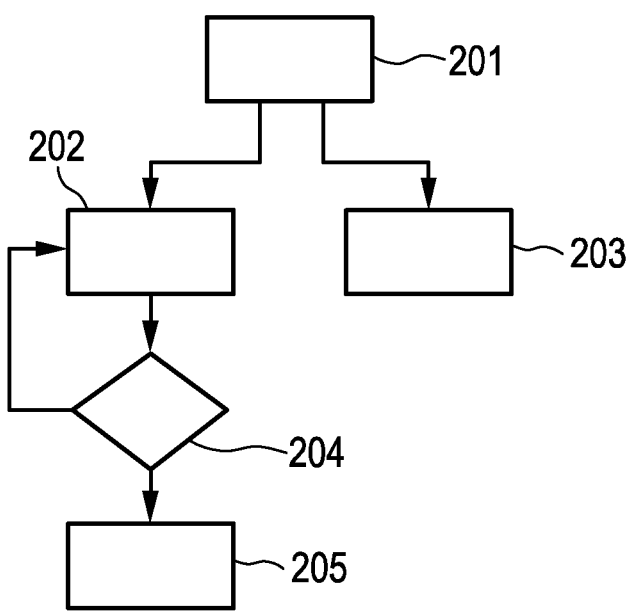
FIG. 9 shows a flowchart exemplarily illustrating a further embodiment of a temperature distribution measuring method for measuring a temperature distribution within an object caused by applying energy to the object.

In the following an embodiment of a temperature distribution measuring method, which uses different first regions at different positions, will exemplarily be described with reference to a flowchart shown in FIG. 9.

In step 201 the tip 5 of the ablation needle 2 is navigated into the liver 20 such that the tip is located within a tumor region within the liver 20. Moreover, in step 201 an initial thermal model is provided by the model providing unit 14. Step 201 is performed in the pre-treatment phase.

Then, in step 203 the treatment starts by applying ablation energy to the tumor region, i.e. by heating the tumor region, and in step 202 a first temperature distribution is measured in a first region 24 within the liver 20 by the temperature distribution measuring unit 13, 71.

In step 204 it is checked whether the first temperature distribution measured in the first region includes a temperature above 50 degrees Celsius, wherein, if this is the case, the temperature measurement continues in step 202 with a further first region having a larger distance to the tip 5 of the ablation needle 2. If the temperature distribution measured in the initial first region does not include a temperature being larger than 50 degrees Celsius, the temperature measurement continues in step 202 with still measuring the temperature distribution in the initial first region. Moreover, the temperatures, which are not larger than 50 degrees Celsius, are provided to the temperature distribution estimating unit 15, wherein in step 205 the temperature distribution estimating unit 15 determines an overall temperature distribution, in particular, determines estimated temperature distributions in the different first regions 24 for time periods, in which a temperature distribution has not been measured in the respective first region, and also in other regions like the second region within the liver 20, in which a temperature distribution has not been measured, by modifying the model parameters of the thermal model such that a deviation of the model temperature distribution in the different first regions for the time periods, in which the respective temperature distribution has been measured in the respective first region, from the already measured temperature distributions in the different first regions is minimized and by determining the estimated temperature distributions from the modified model.

Steps 202 and 204 are performed in a loop, wherein this loop and step 205 are performed in parallel, i.e. the measured temperature distributions are continuously fed to the temperature distribution estimating unit 15, in order to continuously generate an updated overall temperature distribution. The temperature distributions determination steps 202, 204 and 205 on the one side and the ablation step 203 on the other side are also performed in parallel such that during the ablation procedure a user like a physician can monitor the development of the temperature distribution and stop the ablation procedure, if the user is satisfied with the generated temperature distribution. Thus, steps 202 to 205 may be performed until the user stops the procedure or until an abort criterion has been fulfilled.

In this embodiment the first regions 24 have different distances to the tip 5 of the ablation needle 2, i.e. the location, at which the ultrasound measurement is performed, is not stationary. If this location would be stationary, this could result in sub-optimal, for instance, higher or lower, temperatures being measured and the locations could have a high thermal gradient. This would affect the accuracy of the model parameters derived from these measurements in-situ at the ablation site and the estimated therapy end point, which may be reached when a certain thermal dose has been reached, which may be calculated based on the measured temperature distribution.

The temperature distribution measuring procedure described above with reference to FIGS. 8 and 9 provides an adaptive ultrasound thermometry measurement scheme, where the measurement location is changed during the therapy, especially to ensure that an optimal temperature rise, i.e. in this embodiment a temperature rise from 37 to 50 degrees Celsius, is used.

In this embodiment the temperature distribution measuring apparatus 21 is adapted to track the local temperature rise using ultrasound at a couple of planes 24 parallel to the RF ablation tine, i.e. parallel to the heating source. In contrast to the stationary situation in which the temperature is tracked in the same plane at all times, in the dynamic situation as the heating progresses different spatial locations are used to compute the temperature rise.

In this embodiment the temperature distribution measuring apparatus 21 may address the following problems. When the scan plane remains stationary, it cannot be located close to the ablation tine, i.e. the energy application element, because the temperature would increase to beyond 50 degrees Celsius and the measurements would not be useful. If the scan plane is placed far enough to ensure that the temperature rise is never larger than 50 degrees Celsius, the temperature rise could be extremely low at the initial time points and hence the accuracy of the temperature measurement could be reduced. Furthermore, in addition to providing the measured temperature rise using ultrasound to the thermal model, one of the critical inputs is the spatial position where the respective measurement was made with respect to the heating source. When the thermal gradients are high, the uncertainty in the position of the scan plane can result in large errors in the model parameters. The scan plane position may therefore be dynamically modified such that the scan plane is mostly or always in a spatial region with relatively low thermal gradients.

Figure 10:
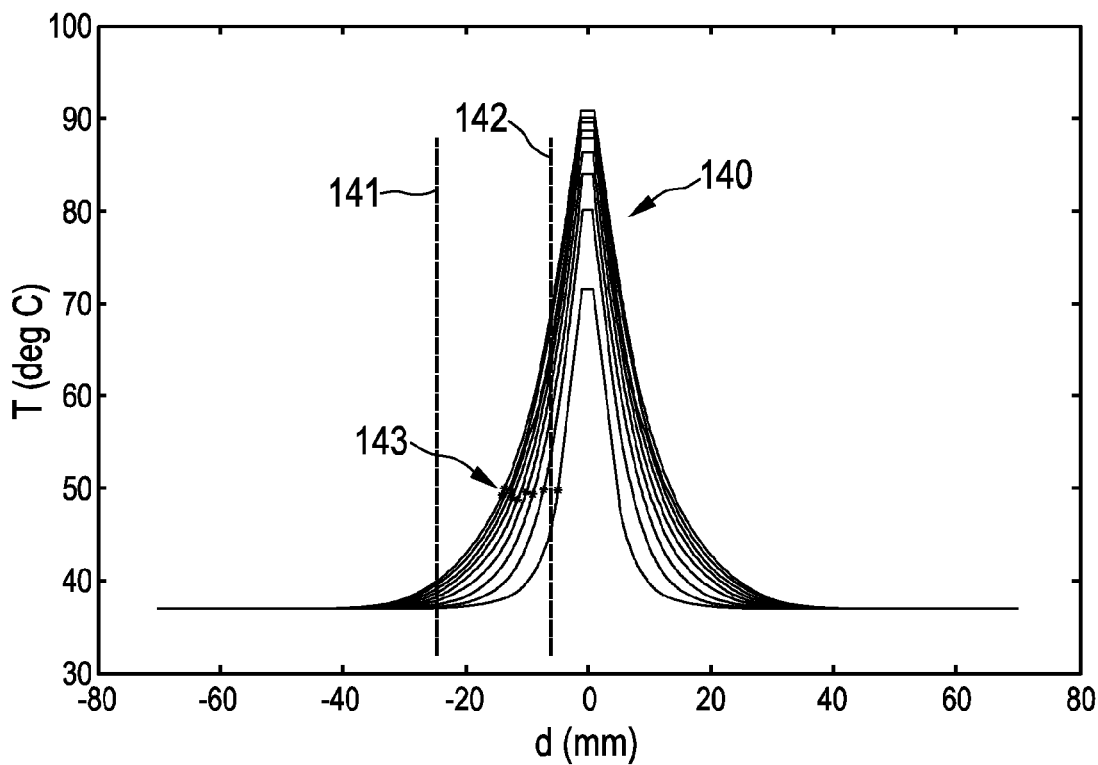
FIG. 10 shows exemplarily a temperature profile.
Figure 11:
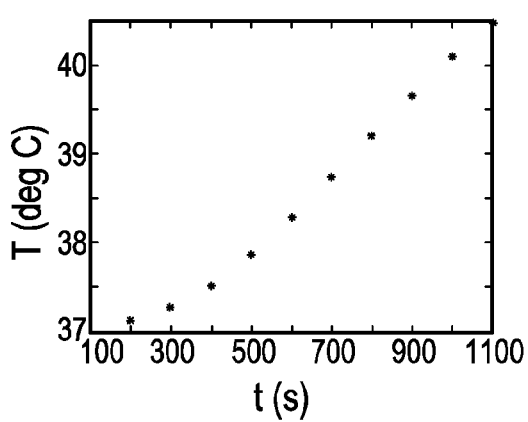
FIG. 11 shows exemplarily an increase of a temperature with time at a distance of 25 mm from an ablation needle.
Figure 12:
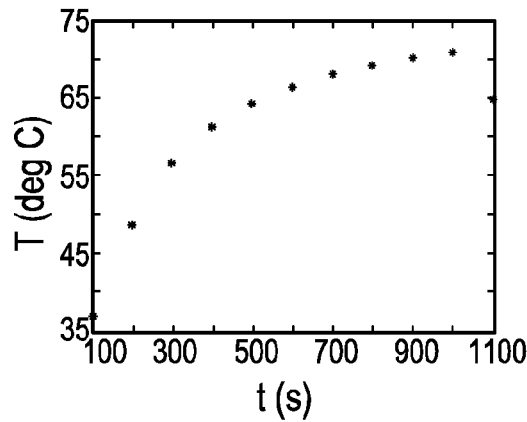
FIG. 12 shows schematically an increase of a temperature with time at a distance of 5 mm from an ablation needle.

FIG. 10 exemplarily illustrates a temperature profile along a line perpendicular to the ablation tine, i.e. to the energy application element, intersecting it at the midpoint of the exposed electrode of the ablation tine. The ablation tine is at the distance d=0 along the horizontal axis. The line plots 140 show the evolution of the temperature T every 100 s during an RF ablation heating procedure in liver tissue. As can be seen in FIG. 10, the peak tine temperature is larger than 90 degrees Celsius. FIG. 11 exemplarily illustrates the temperature evolution at a distance of 25 mm from the position of the heating source, i.e. FIG. 11 exemplarily illustrates the temperatures along the line 141 in FIG. 10. FIG. 12 exemplarily illustrates the temperature evolution at a distance of 5 mm from the position of the heating source, i.e. FIG. 12 shows the temperatures along the line 142 in FIG. 10. These distances, i.e. 5 mm and 25 mm, represent locations where an ultrasound scan plane, i.e. a first region, could be placed in a stationary measurement scheme. However, both locations have disadvantages. At the distance of 25 mm the temperature rise is barely 3.5 degrees Celsius at the end of the therapy as shown in FIG. 11. Thus, at this distance the applicable range of temperatures is not well utilized. At the distance of 5 mm the temperature rises up to a temperature close to 70 degrees Celsius as shown in FIG. 12. This would render ultrasound-based temperature measurement techniques difficult to implement for the above mentioned reasons. These problems illustrated in FIGS. 11 and 12 can be solved by the embodiment with the different first regions at the different positions.

Figure 13:
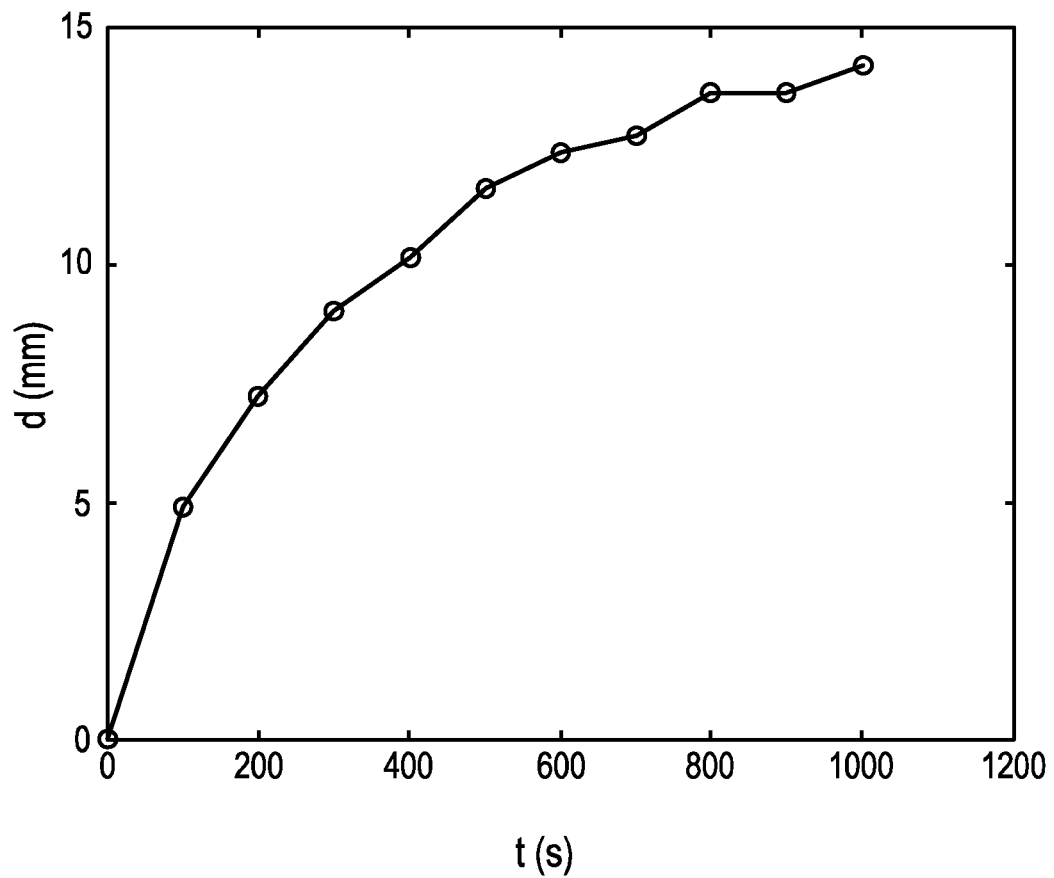
FIG. 13 shows exemplarily positions of first regions depending on time.

In this embodiment the temperature distribution measuring apparatus 21 provides the flexibility to change the position of the first region, i.e. of the ultrasound scan plane, dynamically, which in turn allows to make the ultrasound temperature measurements in the most favorable locations, wherein then these ultrasound temperature measurements can be fed to the thermal model. The optimum positions, i.e. the optimal distances at which the first regions should be placed, can be determined from, for instance, FIG. 13 where the blue asterisks 143 represent the locations at which the temperature is close to 50 degrees Celsius at different time instants. These blue asterisks 143 versus time, i.e. the corresponding distances d versus t, are shown in FIG. 13. FIG. 13 exemplarily illustrates a plot representing distances to the heating source, at which the first regions, i.e. in this embodiment the ultrasound scan planes, could be placed, in order to have an optimal temperature change that can be measured with the ultrasound technique.

In this embodiment the temperature distribution measuring apparatus has the ability to change the position of the scan plane, i.e. of the first region, where the ultrasound thermometry measurement is obtained. The temperature distribution measuring apparatus preferentially comprises an ultrasound probe, which may include a one-dimensional transducer or a two-dimensional transducer. If the ultrasound probe includes a one-dimensional transducer, the ultrasound probe is preferably adapted such that the one-dimensional ultrasound transducer can be mechanically translated to obtain the temperature measurements at the different spatial locations. If the ultrasound probe includes a two-dimensional ultrasound transducer, it has preferentially scan planes positioned at the different locations, at which the ultrasound temperature measurements should be performed. The temperature distribution measuring apparatus preferentially evaluates the temperature measurements at each scan plane location, i.e. in each first region, in order to determine if the temperature rise is within a predefined allowable range, for instance, between 37 degrees Celsius and 50 degrees Celsius. When the temperature rise exceeds beyond this range, the temperature data from that scan plane are rejected and the next distant location is utilized for analysis.

Although in this embodiment a first region, in which temperatures are actually measured, is formed by a single plane only, i.e. although in this embodiment the different first regions are formed by a single movable ultrasound scan plane only, in other embodiments a first region, at which the temperature is actually measured, can be formed by several planes, in particular, by several ultrasound scan planes, such that at the same time the temperature can be measured in different planes. If in at least one of these planes the temperature rises above an upper temperature limit like 50 degrees Celsius, the first region may be modified by excluding this plane from further temperature measurements or by moving this plane to another more distant position. The planes may be vertical or horizontal planes, wherein, if the scan plane is horizontal, it may be scanned in a C-scan manner. Moreover, instead of being planar the first regions can also have another shape, i.e. they can be non-planar, in particular, curved. Moreover, although in above described embodiments the scan planes, i.e. the planar first regions, are parallel to the direction of the ablation tine, in other embodiments they may also be perpendicular to the ablation tine.

If in an embodiment the ultrasound probe comprises a one-dimensional ultrasound transducer, the transducer is preferentially translated mechanically at the start of the treatment to obtain reference ultrasound data at different measurement positions in a reference data acquisition stage, i.e. reference ultrasound data are acquired in the different first regions. Preferentially, the reference sweep in the reference data acquisition stage provides baseline information at a temperature of 37 degrees Celsius. Essentially, this can be regarded as a snapshot of the signature of RF echoes at t=0 before the start of the treatment. The reference ultrasound data can be used during the treatment phase, i.e. during the temperature distribution measurement stage, for determining actual temperature distributions in the different first regions by ultrasound thermometry based on differences between the ultrasound backscatter acquired during the reference data acquisition stage and the actual ultrasound backscatter acquired during the treatment phase.

The distances between the scan positions, i.e. the positions of the planar first regions, can be determined based on a planned target volume of a lesion to be created and the number of required scan planes. Also a priori information from a thermal model, which may be the model provided by the model providing unit 14 and which indicates the thermal gradient at the different positions, may be used to determine the positions of the planar first regions.

After the reference scan has been performed in the reference data acquisition stage, the one-dimensional transducer is repositioned at a first position typically closest to the ablation tine. After the therapy has been started, the temperature rise in the first plane is measured by using a comparison with the corresponding reference frame. The temperature rise measured in this first plane, i.e. in the first region, is continuously fed to the provided thermal model. When the measured temperature in the first plane is close to 50 degrees Celsius, the temperature measurement at this location is stopped and the one-dimensional transducer is moved to the next spatial location, i.e. to the second position, away from the ablation tine. Temperature measurements from the first position will be appended to the subsequent measurements from a second position, from a third position and so forth, and optimal model parameters will be estimated based on these temperature measurements as constraints. Based on the optimal model parameters, i.e. based on the corresponding optimized thermal model, the three-dimensional temperature distribution over the entire volume can be determined.

Although in above described embodiments reference ultrasound data have been acquired in a reference data acquisition stage by performing a reference sweep before the start of the ablation treatment, in other embodiments the temperature distribution measuring method may be performed without such a reference ultrasound data acquisition. In this case the thermal model provided by the model providing unit 14 can be used to determine reference temperatures for measured ultrasound data. In particular, the provided thermal model of the object may describe a model temperature distribution in the first regions, in which the respective temperature distribution has been measured already during the therapy, and in the first regions, in which the respective temperature distribution has not been measured already during the therapy, depending on the modifiable model parameters, wherein the temperature distribution estimation unit may be adapted to determine the reference temperature for a respective first region, in which the respective temperature distribution has not been measured already, by modifying the model parameters such that a deviation of the model temperature distribution in the first regions, in which the respective temperature distribution has been measured already, from the measured temperature distributions in the first regions, in which the respective temperature distribution has been measured already, is minimized and by determining the reference temperature from the modified model. For instance, a one-dimensional ultrasound transducer may be initially placed at the first position from a time $t_0$ up to a time $t_1$, wherein at this first position, i.e. in the corresponding first region, the temperature is measured over time up to the temperature at the time $t_1$. The time $t_1$ may be defined by the time at which the measured temperature is close to, i.e. almost, equal to or just slightly larger than 50 degrees Celsius. Then, the one-dimensional ultrasound transducer is moved to the second position at the time $t_1$, wherein the temperature at the second position, i.e. in a further first region being more distant to the ablation time, at the time $t_1$, i.e. or, to be more specific, at a time $t_1+\Delta t$, wherein $\Delta t$ is the time for moving from the first position to the second position, is predicted from the thermal model based on the already performed temperature measurements in the initial first region. This predicted temperature at the time $t_1$ in the further first region is the reference temperature for the measurement in the further first region and the reference ultrasound data are the ultrasound data acquired at the time $t_1$ in the further first region. After the one-dimensional transducer has been moved to the second position, the temperature rise measured at this location from the time $t_1$ to the time $t_2$ is added to the starting temperature derived from the thermal model at the time $t_1$ to obtain the absolute temperature at the time $t_2$. The same procedure can be performed for further, more distant first regions and corresponding time intervals $t_2$ to $t_3$, $t_3$ to $t_4$, $t_4$ to $t_5$ et cetera. As data are available at different spatial positions away from the ablation time, very robust data are provided for estimating thermal parameters that determine the spatial-temporal heat distribution profile.

If instead of a one-dimensional ultrasound transducer a two-dimensional ultrasound transducer, i.e. a two-dimensional ultrasound array, is used, the ability to image in multiple two-dimensional scan planes is provided. The scan planes, in which the data will be acquired, i.e. the corresponding positions and thus the first regions, are preferentially predefined. The ultrasound data acquired in these predefined scan planes can be processed sequentially starting from scan planes closest to the ablation tine at a time $t_0$ and progressively further away at later times. The ultrasound data acquired at each of these spatial locations, i.e. in each of the planar first regions, can be used to determine the temperature distributions in these first regions by ultrasound thermometry and the determined temperature distributions can be fed to the thermal model to estimate the model parameters and the resulting overall temperature distribution. Since in this embodiment a two-dimensional ultrasound transducer is used, in a reference data acquisition stage the reference frames, i.e. the reference ultrasound data for the different first regions at the time $t_0$, i.e. when the temperature of the person is 37 degrees Celsius, are easily simultaneously available.

Although in above described embodiments the temperature distribution determining technique is used in connection with an RF ablation procedure, in other embodiments the temperature distribution determining technique can also be used together with other energy application procedures like other ablation procedures. For instance, the temperature distribution determining technique may also be combined with HIFU, microwave ablation, laser ablation et cetera.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the determination of the first temperature distribution depending on acquired ultrasound data, the provision of the model, the estimation of the second temperature distribution based on the first temperature distribution and the provided model, etc. performed by one or several units or devices can be performed by any other number of units or devices. These procedures and/or the control of the temperature distribution determining apparatus in accordance with the temperature distribution determining method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a temperature distribution determining apparatus for determining a temperature distribution within an object, to which energy is applied, by using an energy application element. A first temperature distribution is measured in a first region within a first temperature range and a model describing a model temperature distribution in the first region and in a second region depending on modifiable model parameters is provided. A second temperature distribution is estimated in the second region within a second temperature range, while the energy is applied to the object, by modifying the model parameters such that a deviation of the model temperature distribution from the first temperature distribution in the first region is minimized. This allows considering the temperature dependence of the model parameters within the second temperature range, while estimating the second temperature distribution, thereby improving the accuracy of the estimation of the second temperature distribution.

The invention claimed is:
1. A temperature distribution determining apparatus for determining a temperature distribution within an object caused by applying energy to the object, wherein the energy is applied by using an energy application element, wherein the energy application element is adapted to measure the temperature at the energy application element, the temperature distribution determining apparatus comprising:
- an ultrasound thermometry unit for determining a first temperature distribution in a first region within the object within a predetermined first temperature range, while the energy is applied to the object by the energy application element for heating the object, based on ultrasound data of the first region acquired by an ultrasound probe, wherein a temperature distribution measuring unit comprises the ultrasound thermometry unit and the ultrasound probe,
- a model providing unit for providing a model describing a model temperature distribution in the first region, in a second region within the object and at the energy application element depending on modifiable model parameters, wherein the second region is closer to the energy application element than the first region, and
- a temperature distribution estimating unit for estimating a second temperature distribution in the second region within a second temperature range, which is different from the first temperature range, while the energy is applied to the object, by modifying the modifiable model parameters such that a deviation of the model temperature distribution from the first temperature distribution in the first region is minimized and a deviation of the model temperature distribution from the temperature measured at the energy application element is minimized.

2. The temperature distribution determining apparatus as defined in claim 1, wherein the temperature distribution measuring unit further comprises a fixture for fixing the ultrasound probe to the energy application element.

3. The temperature distribution determining apparatus as defined in claim 1, wherein the ultrasound probe is adapted to acquire the ultrasound data in two planes being orthogonal to each other and defining the first region.

4. The temperature distribution determining apparatus as defined in claim 1, wherein the modifiable model parameters include thermal parameters and/or electrical parameters.

5. The temperature distribution determining apparatus as defined in claim 1, wherein the model providing unit is adapted to initialize the provided model with initial model parameters, wherein at least one initial model parameter is an object-specific model parameter.

6. The temperature distribution determining apparatus as defined in claim 1, wherein the object is a living being and the energy is applied by the energy application element to the living being for ablating a part of the living being, wherein the temperature distribution determining apparatus further comprises an ablated region determining unit for determining an ablated region defining a region within the object that has been ablated, wherein the ablated region determining unit is adapted to determine the ablated region by determining a part of the object for which the estimated second temperature distribution comprises a temperature being larger than a predefined temperature threshold.

7. The temperature distribution determining apparatus as defined in claim 6, wherein the temperature distribution determining apparatus further comprises a region of interest providing unit for providing a region of interest, which should be ablated, and a display for displaying the determined ablated region and the provided region of interest.

8. The temperature distribution determining apparatus as defined in claim 1, wherein the temperature distribution measuring unit is adapted to modify the first region depending on the measured first temperature distribution, in order to measure different first temperature distributions in different first regions in the predetermined first temperature range, wherein the model providing unit is adapted to provide the model such that it describes a model temperature distribution in the different first regions and in the second region within the object depending on the modifiable model parameters and wherein the temperature distribution estimating unit is adapted to estimate the second temperature distribution in the second region within the second temperature range, while the energy is applied to the object, by modifying the modifiable model parameters such that a deviation of the model temperature distribution from the first temperature distributions in the different first regions is minimized.

9. The temperature distribution determining apparatus as defined in claim 8, wherein the temperature distribution measuring unit is adapted to modify the first region by changing a position of the first region.

10. The temperature distribution determining apparatus of claim 1, wherein the predetermined first temperature range of the first region is less than 50 degrees Celsius, and the second temperature range of the second region is greater than 50 degrees Celsius.

11. A system for applying energy to an object, the system comprising:
- the energy application element for applying the energy to the object, and
- the temperature distribution determining apparatus as defined in claim 1 for determining a temperature distribution within the object caused by applying the energy to the object.

12. The system as defined in claim 11, wherein the system further comprises:
- an ablation energy control unit for controlling application of the energy by the energy application element depending on the determined temperature distribution.

13. A temperature distribution determining method for determining a temperature distribution within an object caused by applying energy to the object, wherein the energy is applied by using an energy application element, the temperature distribution determining method comprising:
- inserting the energy application element into the object,
- measuring a first temperature distribution in a first region within the object within a predetermined first temperature range, while the energy is applied to the object using the energy application element, by a temperature distribution measuring unit, wherein the temperature distribution measuring unit comprises an ultrasound probe acquiring ultrasound data of the first region and an ultrasound thermometry unit determining the first temperature distribution based on the acquired ultrasound data, and measuring a temperature at the energy application element,
- providing a model describing a model temperature distribution in the first region, in a second region within the object and at the energy application element depending on modifiable model parameters, wherein the second region is closer to the energy application element than the first region, by a model providing unit,
- estimating a second temperature distribution in the second region within a second temperature range, which is different from the first temperature range, while the energy is applied to the object, by modifying the modifiable model parameters such that a deviation of the model temperature distribution from the first temperature distribution in the first region is minimized and a deviation of the model temperature distribution from the temperature measured at the energy application element is minimized by a temperature distribution estimating unit.

14. The method of claim 13, wherein the object is a person.

15. A computer readable medium storing a computer program, executable by a computer processor, for determining method for a temperature distribution within an object caused by applying energy to the object, wherein the energy is applied by using an energy application element inserted into the object, the computer readable medium comprising:

measuring code segment for measuring a first temperature distribution in a first region within the object within a first temperature range, while the energy is applied to the object by the energy application element, using an ultrasound thermometry unit that determines the first temperature distribution based on ultrasound data of the first region acquired by an ultrasound probe, and measuring the temperature at the energy application element, providing a model describing a model temperature distribution in the first region, in a second region within the object and at the energy application element depending on modifiable model parameters, wherein the second region is closer to the energy application element than the first region, by a model providing unit, estimating a second temperature distribution in the second region within a second temperature range, which is different from the first temperature range, while the energy is applied to the object, by modifying the modifiable model parameters such that a deviation of the model temperature distribution from the first temperature distribution in the first region is minimized and a deviation of the model temperature distribution from the temperature measured at the energy application element is minimized by a temperature distribution estimating unit.

* * * * *